(12) United States Patent
Dupret et al.

(10) Patent No.: US 7,718,786 B2
(45) Date of Patent: *May 18, 2010

(54) PROCESS FOR OBTAINING RECOMBINED NUCLEOTIDE SEQUENCES IN VITRO, LIBRARIES OF SEQUENCES AND SEQUENCES THUS OBTAINED

(75) Inventors: Daniel Dupret, Calvisson (FR); Jean-Michel Masson, Toulouse (FR); Fabrice Lefevre, Nimes (FR)

(73) Assignee: Proteus SA, Nimes (FR)

( * ) Notice: Subject to any disclaimer, the term of this patent is extended or adjusted under 35 U.S.C. 154(b) by 121 days.

This patent is subject to a terminal disclaimer.

(21) Appl. No.: 11/143,455

(22) Filed: Jun. 3, 2005

(65) Prior Publication Data
US 2005/0221378 A1 Oct. 6, 2005

Related U.S. Application Data

(63) Continuation of application No. 09/723,316, filed on Nov. 28, 2000, now Pat. No. 6,951,719, which is a continuation of application No. PCT/FR99/01973, filed on Aug. 11, 1999.

(51) Int. Cl.
*C07H 21/02* (2006.01)
*C12Q 1/68* (2006.01)
(52) U.S. Cl. .......................... 536/23.1; 435/6
(58) Field of Classification Search ............. 435/320.1, 435/6; 536/23.1, 22.1
See application file for complete search history.

(56) References Cited

U.S. PATENT DOCUMENTS

| | | | |
|---|---|---|---|
| 4,500,640 A | 2/1985 | Katsumata et al. | |
| 5,605,793 A | 2/1997 | Stemmer | |
| 5,614,389 A | 3/1997 | Auerbach | |
| 5,650,271 A | 7/1997 | Richards | |
| 5,830,721 A | 11/1998 | Stemmer et al. | |
| 5,837,458 A | 11/1998 | Minshull et al. | |
| 5,874,283 A | 2/1999 | Harrington et al. | |
| 6,013,456 A | 1/2000 | Akhavan-Tafti | |
| 6,096,548 A | 8/2000 | Stemmer | |
| 6,117,679 A | 9/2000 | Stemmer | |
| 6,132,970 A | 10/2000 | Stemmer | |
| 6,143,527 A * | 11/2000 | Pachuk et al. | 435/91.1 |
| 6,153,410 A | 11/2000 | Arnold et al. | |
| 6,159,690 A * | 12/2000 | Borrebaeck et al. | 435/6 |
| 6,165,793 A | 12/2000 | Stemmer | |
| 6,171,820 B1 | 1/2001 | Short | |
| 6,177,263 B1 | 1/2001 | Arnold et al. | |
| 6,180,406 B1 | 1/2001 | Stemmer | |
| 6,238,884 B1 | 5/2001 | Short et al. | |
| 6,251,649 B1 | 6/2001 | Matsui et al. | |
| 6,251,674 B1 | 6/2001 | Tobin et al. | |
| 6,277,638 B1 | 8/2001 | Stemmer | |
| 6,287,861 B1 | 9/2001 | Stemmer et al. | |
| 6,287,862 B1 | 9/2001 | delCardayre et al. | |
| 6,291,165 B1 | 9/2001 | Borchert et al. | |
| 6,291,242 B1 | 9/2001 | Stemmer | |
| 6,297,053 B1 | 10/2001 | Stemmer | |
| 6,303,344 B1 | 10/2001 | Patten et al. | |
| 6,309,883 B1 | 10/2001 | Minshull et al. | |
| 6,319,713 B1 | 11/2001 | Patten et al. | |
| 6,319,714 B1 | 11/2001 | Crameri et al. | |
| 6,322,969 B1 | 11/2001 | Stull et al. | |
| 6,323,030 B1 | 11/2001 | Stemmer | |
| 6,326,204 B1 | 12/2001 | delCardayre et al. | |
| 6,335,160 B1 | 1/2002 | Patten et al. | |
| 6,335,198 B1 | 1/2002 | delCardayre et al. | |
| 6,337,186 B1 | 1/2002 | Krebber | |
| 6,344,356 B1 | 2/2002 | Stemmer | |
| 6,348,314 B1 | 2/2002 | Prudent et al. | |
| 6,352,842 B1 | 3/2002 | Short et al. | |
| 6,355,484 B1 | 3/2002 | Patten et al. | |
| 6,358,709 B1 | 3/2002 | Short et al. | |
| 6,358,740 B1 | 3/2002 | Patten et al. | |
| 6,361,974 B1 | 3/2002 | Short et al. | |
| 6,365,377 B1 | 4/2002 | Patten et al. | |
| 6,365,408 B1 | 4/2002 | Stemmer | |
| 6,368,861 B1 | 4/2002 | Crameri et al. | |
| 6,372,497 B1 | 4/2002 | Stemmer | |
| 6,376,246 B1 | 4/2002 | Crameri et al. | |
| 6,387,620 B1 | 5/2002 | Smith et al. | |

(Continued)

FOREIGN PATENT DOCUMENTS

EP 0752008 1/1997

(Continued)

OTHER PUBLICATIONS

Rouwendal et al., "Simultaneous Mutagensis of Multiple Sites: Application of the Ligase Chain Reaction Using PCR Products Instead of Oligonucleotides," Biotechniques, Vo. 15, No. 1, Jul. 1993, pp. 172-178.

(Continued)

*Primary Examiner*—Suryaprabha Chunduru
(74) *Attorney, Agent, or Firm*—Hunton & Williams LLP

(57) ABSTRACT

Ligation-mediated method of recombining polynucleotides in vitro. Polynucleotides from a library are fragmented and the fragments are hybridized to an assembly template. The hybridized fragments are iteratively re-hybridized and ligated until the ends of the hybridized fragments are adjacent to the ends of other hybridized fragments on the assembly template. A final ligation produces recombined polynucleotides.

3 Claims, 9 Drawing Sheets

U.S. PATENT DOCUMENTS

| | | | |
|---|---|---|---|
| 6,406,855 B1 | 6/2002 | Patten et al. | |
| 6,420,175 B1 | 7/2002 | Stemmer | |
| 6,426,224 B1 | 7/2002 | Crameri et al. | |
| 6,444,468 B1 | 9/2002 | Stemmer et al. | |
| 6,455,253 B1 | 9/2002 | Patten et al. | |
| 6,479,652 B1 | 11/2002 | Crameri et al. | |
| 6,482,647 B1 | 11/2002 | Stemmer | |
| 6,518,065 B1 | 2/2003 | Stemmer | |
| 6,537,776 B1 | 3/2003 | Short | |
| 6,605,449 B1 | 8/2003 | Short | |
| 6,951,719 B1 * | 10/2005 | Dupret et al. | 435/6 |
| 6,991,922 B2 * | 1/2006 | Dupret et al. | 435/91.1 |
| 2001/0039014 A1 | 11/2001 | Bass et al. | |
| 2001/0049104 A1 | 12/2001 | Stemmer et al. | |
| 2002/0142394 A1 | 10/2002 | Short | |
| 2003/0027156 A1 | 2/2003 | Patten | |
| 2003/0036116 A1 | 2/2003 | Short | |
| 2003/0054390 A1 | 3/2003 | Crameri et al. | |
| 2003/0092023 A1 | 5/2003 | Dupret et al. | |
| 2003/0104417 A1 | 6/2003 | Dupret et al. | |
| 2004/0191772 A1 | 9/2004 | Dupret et al. | |

FOREIGN PATENT DOCUMENTS

| | | |
|---|---|---|
| EP | 1138763 | 2/2002 |
| FR | 2782323 | 2/2000 |
| JP | 11075849 | 3/1999 |
| WO | WO 95/22625 | 8/1995 |
| WO | WO 97/20078 | 6/1997 |
| WO | WO 97/22715 | 6/1997 |
| WO | WO 97/42330 | 11/1997 |
| WO | WO 98/15567 | 4/1998 |
| WO | WO 9813485 A1 * | 4/1998 |
| WO | WO 98/27230 | 6/1998 |
| WO | WO 98/32845 | 7/1998 |
| WO | WO 00/58517 | 10/2000 |
| WO | WO 00/77262 | 12/2000 |
| WO | WO 01/81568 | 3/2001 |
| WO | WO 01/23401 | 4/2001 |
| WO | WO 01/27160 | 4/2001 |
| WO | WO 01/29211 | 4/2001 |
| WO | WO 01/29212 | 4/2001 |
| WO | WO 01/42509 | 6/2001 |
| WO | WO 01/51663 | 7/2001 |
| WO | WO 01/64864 | 9/2001 |
| WO | WO 01/70947 | 9/2001 |
| WO | WO 01/73000 | 10/2001 |
| WO | WO 01/90346 | 11/2001 |
| WO | WO 01/96551 | 12/2001 |
| WO | WO 02/04629 | 1/2002 |
| WO | WO 02/06469 | 1/2002 |

OTHER PUBLICATIONS

Stemmer, W. P. C., "DNA shuffling by random fragmentation and reassembly: In vitro recombination for molecular evolution", Proc. Natl. Acad. Sci. USA, vol. 91, pp. 10747-10751, Oct. 1994.

Punnonen, J. et al., "Molecular breeding by DNA shuffling", Science & Medicine, pp. 38-47, Mar./Apr. 2000.

Coco, W. M. et al., "DNA shuffling method for generating highly recombined genes evolved enzymes", Nature Biotechnology, vol. 15, Apr. 2001, pp. 354-358.

Pelletier, J., "A rachitt for our toolbox", Nature Biotechnology, vol. 19, No. 4, Apr. 2001, pp. 314-315.

Crameri, A. et al., "DNA shuffling of a family of genes from diverse species accelerates directed evolution", Nature, vol. 391, Jan. 1998, pp. 288-291.

Ness, J. E. et al., "DNA shuffling of subgenomic sequences of subtilisin", Nature Biotechnology, vol. 17, Sep. 1999, pp. 893-896.

Chang, C. J. et al., "Evolution of a cytokine using DNA family shuffling", Nature Biotechnology, vol. 17, Aug. 1999, pp. 793-797.

Minshull, J. et al., "Protein evolution by molecular breeding", Current Opinion in Chemical Biology, 1999, vol. 3, pp. 284-290.

Harayama, S. "Artificial evolution by DNA shuffling", Tibtech, Feb. 1998, vol. 16, pp. 76-82.

Kurtzman, A., "Advances in directed protein evolution by recursive genetic recombination: applications to therapeutic proteins", Current Opinion in Biotechnology, 2001, vol. 12, pp. 361-370.

Zhao, H. et al., "Optimization of DNA Shuffling for High Fidelity Recombination", Nucleic Acids Research, vol. 25, No. 6, pp. 1307-1308, (1997).

Zhao, H. et al., "Molecular Evolution by Staggered Extension Process (StEP) In Vitro Recombination", Nature Biotechnology, vol. 16, pp. 258-261 (1998).

Lyamichev, V. et al., "Polymorphism Identification and Quantitative Detection of Genomic DNA by Invasive Cleavage of Oligonucleotide Probes", Nature Biotechnology, vol. 17, pp. 292-296 (1999).

Gary et al., "The DNA Repair Enodnuclease XPG Binds to Proliferating Cell Nuclear Antigen (PCNA) and Shares Sequence Elements with the PCNA-binding Regions of FEN-1", The Journal of Biological Chemistry, 1997, vol. 39, pp. 24552-24529.

Michnick, S. et al., "'Itching' for New Strategies in Protein Engineering," Nature Biotechnology, vol. 17, pp. 1159-1160 (1999).

Carter, P. et al., "Antibody Engineering Using Very Long Template-Assembled Oligonucleotides," Methods: A Companion to Methods in Enzymology, vol. 3, No. 3, pp. 183-192 (1991).

Nickerson, D., et al., "Automated DNA diagnostics using an ELISA-based oligonucleotide ligation assay," Proc. Natl. Acad. Sci. USA 87:8923-8927 (1990).

New England Biolabs, Inc., "T4 DNA Ligase," Technical Bulletin #M0202 (Jul. 31, 2006), available at http://www.neb.com/nebecomm/TechBulletinFiles/techbulletinM0202.pdf.

Definition of thermostable, Merriam-Webster Online Dictionary, at http://www.m-w.com/dictionary/thermostable (Apr. 30, 2007).

* cited by examiner

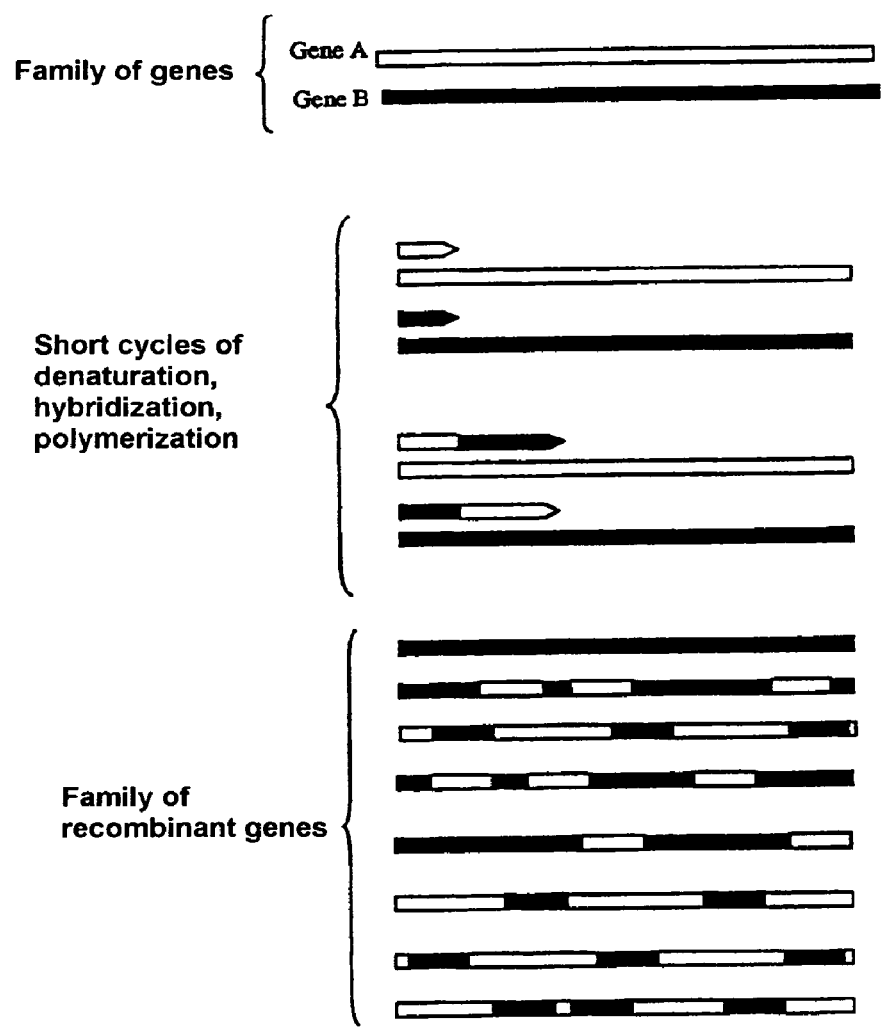

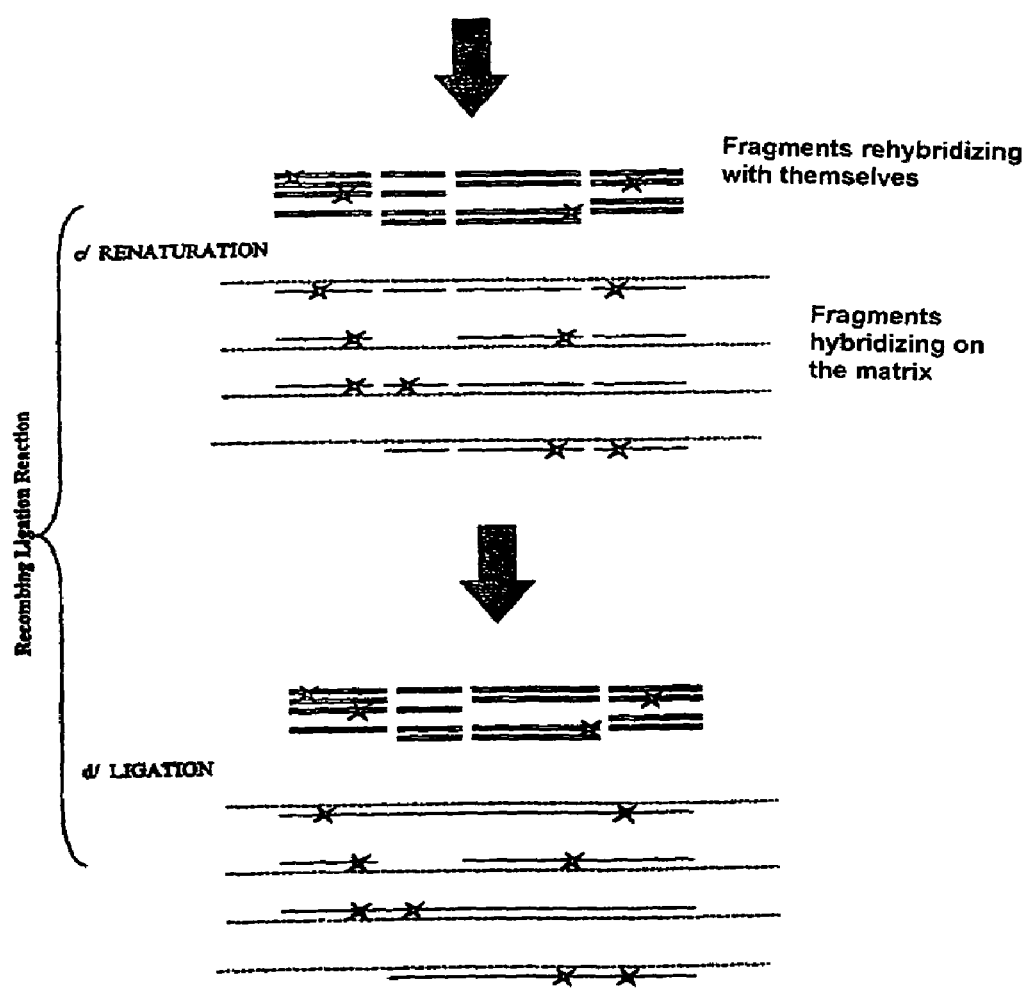
Fig. 2- continued

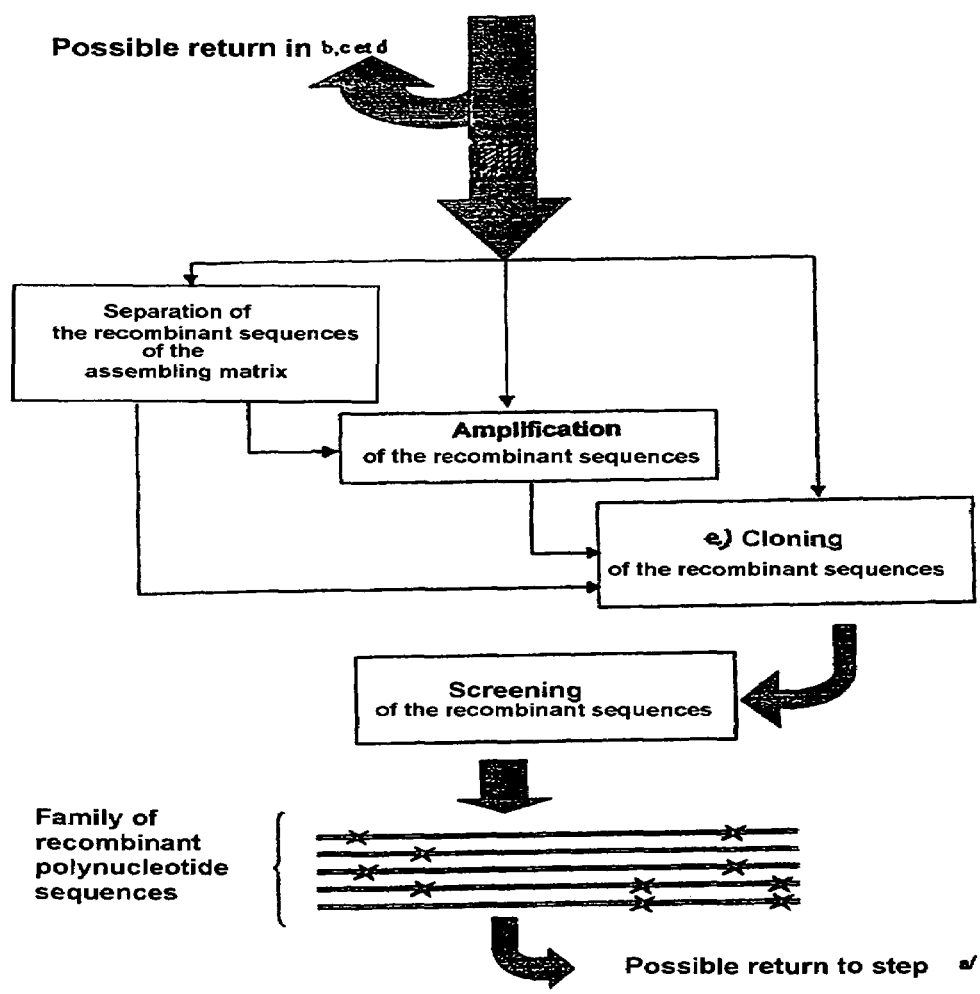

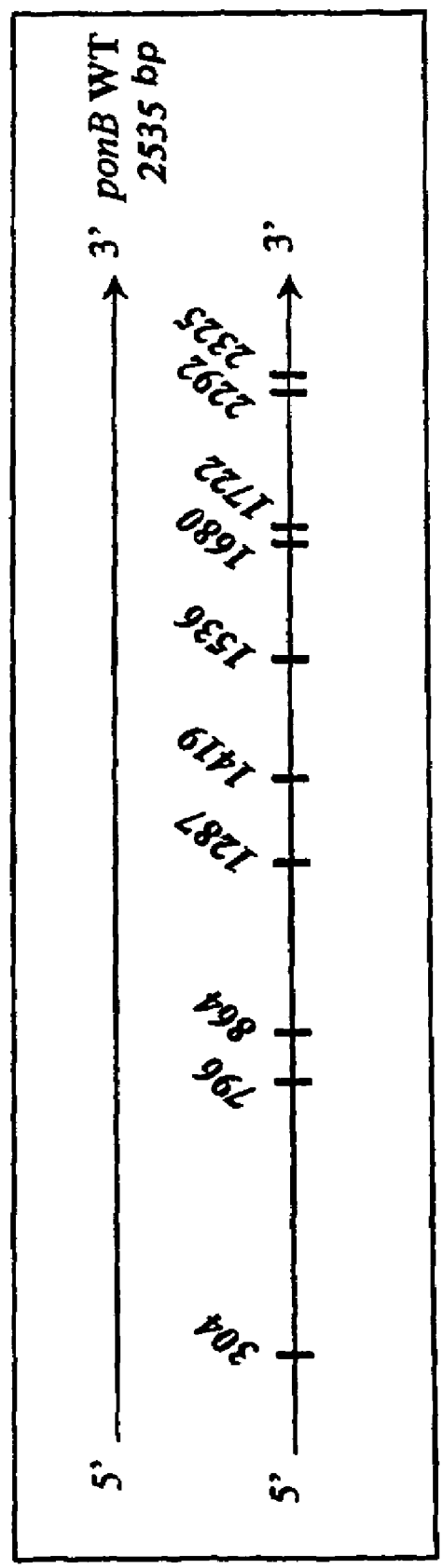
Figure 3: Position of the ten mutation zones (sites Pvu II and Pst I)

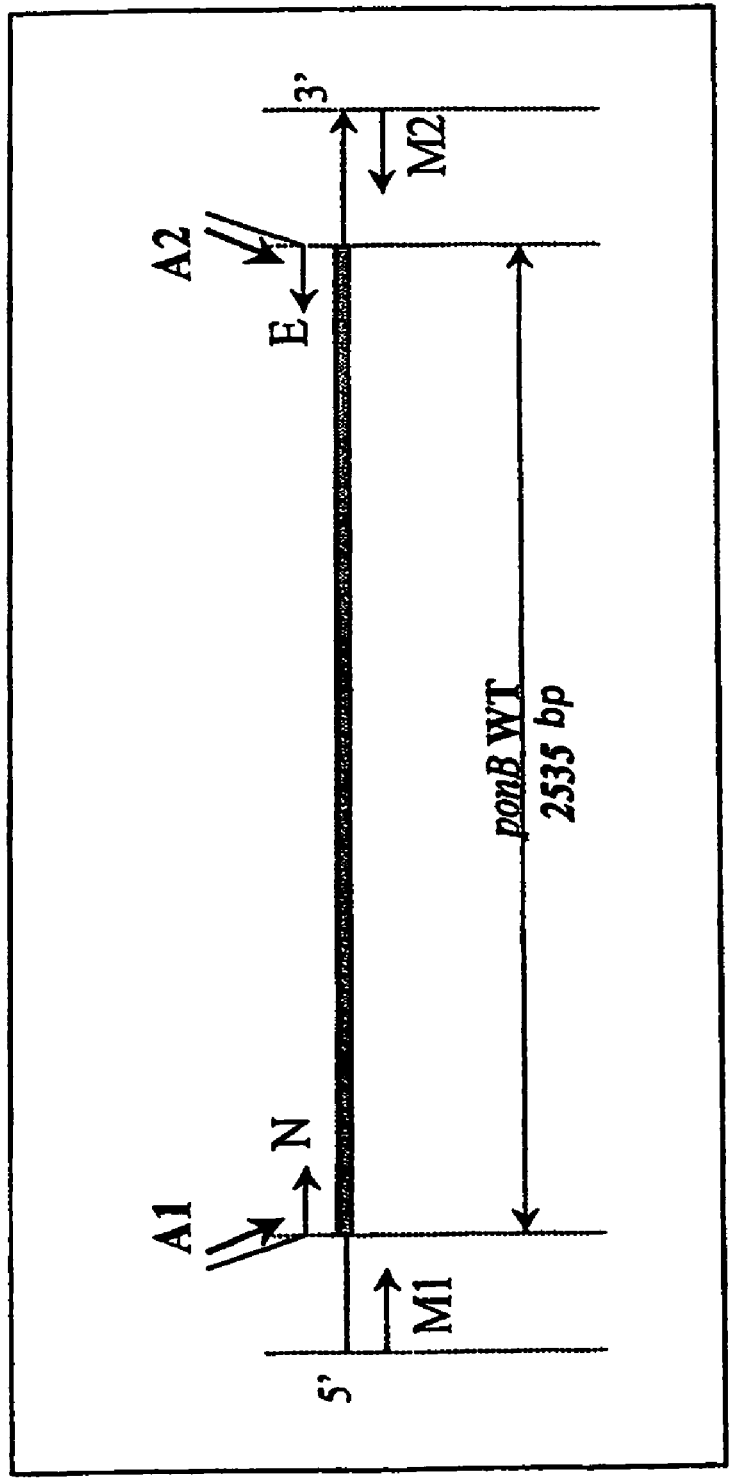
Figure 4: Position of the primers used as compared to the sequence of the ponB gene

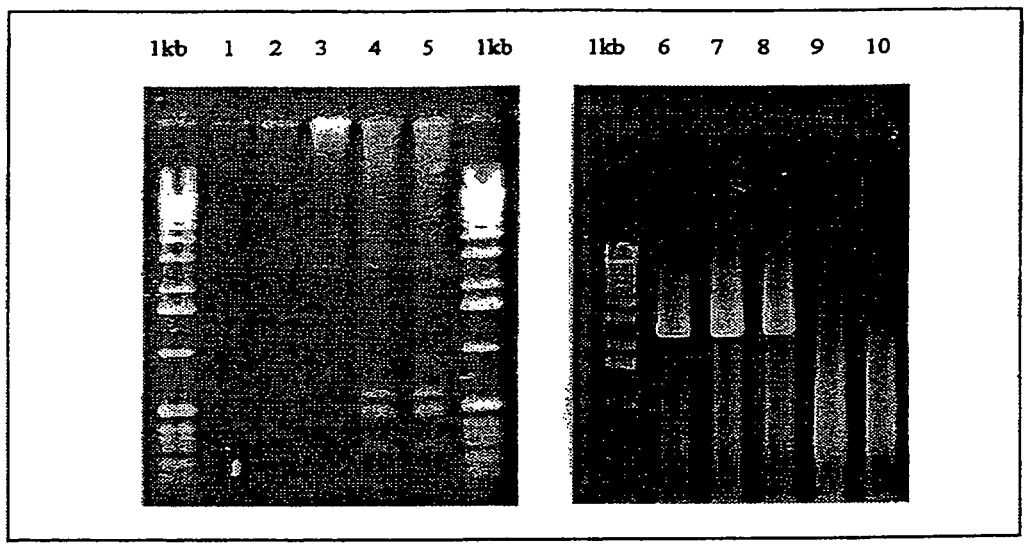
Fig. 5 : Migration of the RLR reactions and of the PCR amplifications of these reactions
Tracks:
1/ RLR 1
2/ RLR 2
3/ RLR 3
4/ RLR 4
5/ RLR Control
6/ PCR RLR 1
7/ PCR RLR 2
8/ PCR RLR 3
9/ PCR RLR 4
10/ PCR RLR Control

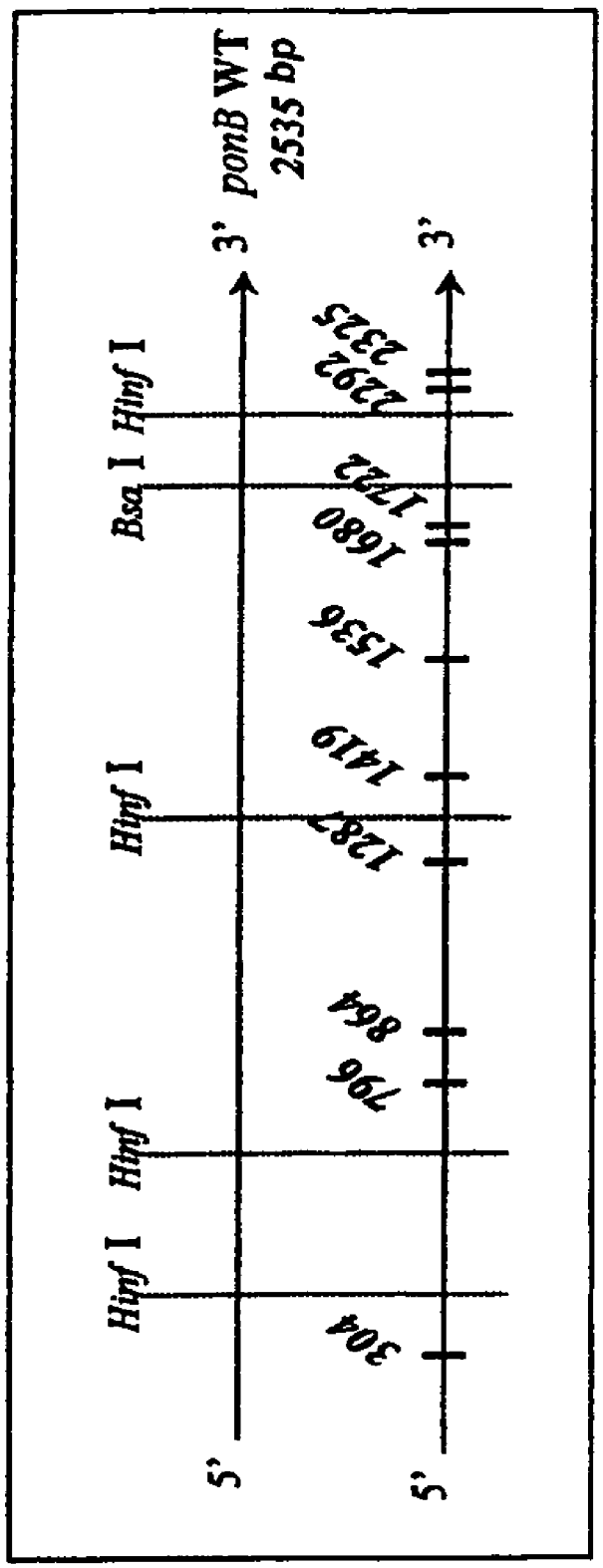
Figure 6 : Position of the mutations as compared to the restriction fragments

SEQUENCE LISTING

```
<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Oligo N

<400> SEQUENCE: 1
actgactacc atggccggga atgaccgcga gcc                              33

<210> SEQ ID NO 2
<211> LENGTH: 39
<212> TYPE: DNA
<213> ORGANISM: Artificial Sequence
<220> FEATURE:
<223> OTHER INFORMATION: Oligo E

<400> SEQUENCE: 2
ccgcggtgga gcgaattcta attactacca aacatatcc                        39

<210> SEQ ID NO 3
<211> LENGTH: 26
<212> TYPE: DNA
<213> ORGANISM: Artificial Sequence
<220> FEATURE:
<223> OTHER INFORMATION: Oligo M1

<400> SEQUENCE: 3
gcgcctgaat attgcggaga aaaagc                                      26

<210> SEQ ID NO 4
<211> LENGTH: 30
<212> TYPE: DNA
<213> ORGANISM: Artificial Sequence
<220> FEATURE:
<223> OTHER INFORMATION: Oligo M2

<400> SEQUENCE: 4
acaaccagat gaaaagaaag ggttaatatc                                  30

<210> SEQ ID NO 5
<211> LENGTH: 16
<212> TYPE: DNA
<213> ORGANISM: Artificial Sequence
<220> FEATURE:
<223> OTHER INFORMATION: Oligo A1

<400> SEQUENCE: 5
```

```
actgactacc atggcc                                               16

<210> SEQ ID NO 6
<211> LENGTH: 18
<212> TYPE: DNA
<213> ORGANISM: Artificial Sequence
<220> FEATURE:
<223> OTHER INFORMATION: Oligo A2

<400> SEQUENCE: 6
ccgcggtgga gcgaattc                                             18
```

PROCESS FOR OBTAINING RECOMBINED NUCLEOTIDE SEQUENCES IN VITRO, LIBRARIES OF SEQUENCES AND SEQUENCES THUS OBTAINED

CROSS-REFERENCE TO RELATED APPLICATIONS

This application is a continuation of U.S. patent application Ser. No. 09/723,316, filed Nov. 28, 2000, which is a continuation of PCT International Application No. PCT/FR99/01973, filed Aug. 11, 1999, which claims priority to French Patent Application No. FR98/10338, filed Aug. 12, 1998. All of the foregoing applications are incorporated by reference herein in their entireties.

The present invention relates to a method of obtaining recombined nucleotide sequences in vitro. The invention is particularly aimed at generating and then selecting polynucleotide sequences which are liable to have one or several advantageous properties as compared to the corresponding properties of reference sequences and therefore capable of conferring an improved phenotype and/or of producing improved proteins.

By reference sequence is understood a sequence having properties close to those being sought.

Different techniques have been developed in order to favor the in vitro recombination between different polynucleotide sequences, among which can be more particularly cited DNA-shuffling (12) and StEP (14), both based on the use of PCR.

DNA-Shuffling comprises two steps, the random fragmenting by DNAse I of polynucleotide sequences, and an amplification by PCR in which the fragments previously generated serve as primers. At each step of hybridization, the change of template provokes recombinations at the level of the regions having homologous sequences. A schematic representation of this method is provided in FIG. 1A.

The step consists of mixing different polynucleotide sequences containing various mutations in the presence of a pair of primers. This mixture is subjected to a PCR type of reaction in which the hybridization and polymerization steps are grouped together in a single step of very short duration. These conditions permit hybridization of primers but reduce the duration hence the length of polymerization, in such a way that the fragments which are partially synthesized are randomly hybridized to the polynucleotide sequences having different mutations, thus permitting the recombination. A schematic representation of this method is provided at FIG. 1B.

In each of these two methods, the polymerization step is indispensable to the process of recombination. Thus, according to the polymerase chosen, this polymerization step can bring about undesired supplemental mutations. Moreover, the DNA-shuffling and the step procedures rest on the principle of the hybridization of a "mega-primer" (6) to a template, which likely leads to difficulties in implementation for polynucleotide sequences of size greater than 1.5 kbp (11). Finally, these two techniques do not permit the control of the rate of recombination, since they are made randomly in the course of successive polymerization steps.

The present invention solves the disadvantages described above by offering a simple method for the preparation of recombined polynucleotide sequences, permitting the generation of polynucleotide sequences capable of displaying advantageous properties as compared to the corresponding properties of the sequences of reference and therefore capable of conferring an improved phenotype and/or producing improved proteins.

This goal is attained thanks to a in vitro process for obtaining recombined nucleotide sequences starting from a library of polynucleotide sequences, also designated hereinafter as the initial library, characterized in that it includes the following steps:
 a) fragmenting a library of double-stranded polynucleotide sequences,
 b) the denaturation of fragments possibly in the presence of one or several assembling templates,
 c) the hybridization of said fragments with one or several assembling templates if the template/templates is/are not present in step (b),
 d) the ligation of said fragments in order to obtain recombined polynucleotide sequences,
 e) the selection of recombined nucleotide sequences having advantageous properties as compared to the corresponding properties of one or several reference sequences.

The process of the invention can include at the output of step (d) and before step (e), the repeating of steps (b), (c) and (d) no longer with the fragments of step (a) but with the products of step (d).

This embodiment is particularly useful in the case where, at the outlet of step (d) all the fragments are not ligated. In this case, the process of the invention moreover includes, at the end of step (d) and before step (e), one or several of the following reaction cycles:
 denaturation of the ligated and non-ligated fragments coming out of step (d), possibly in the presence of one or several assembling templates.
 hybridization of said fragments with one or several assembling templates if it (they) is (are) not present at the time of the denaturation,
 ligation of said fragments.

These denaturation, hybridization and ligation reactions are equivalent in steps (b), (c) and (d) but carried out not with the fragments of step (a) but with the ligated and non-ligated fragments coming out of step (d).

The process of the invention can moreover include one or several of the following steps:
 the separation of the recombined polynucleotide sequences from the assembling template or templates before step (e),
 the amplification of the double-stranded recombined polynucleotide sequences before step (e).
 the cloning of the recombined polynucleotide sequences possibly after separation of the recombined strands from the template or templates and obtaining of the corresponding double strand before step (e).

The ends of the fragments generated at step (a) are such that there can be adjacent hybridization of these ends to the assembling template or templates at step (c) and ligation of these fragments with each other at step (d). The polynucleotide sequences of the library on which the process of the invention is carried out must include zones of homology either between them or with the assembling templates, so as to permit the generating of the ends of the fragments such as described above.

One advantageous embodiment of the process of the invention consists in simultaneously carrying out steps (c) and (d) according to a reaction called RLR for the English expression of "Recombining Ligation Reaction."

Besides the advantages previously indicated, the process of the invention is notable in that it favors and accelerates the random recombination in vitro of polynucleotide sequences and these polynucleotide sequences can be genes. By gene is understood a DNA fragment or sequence associated with a biological function. A gene can be obtained in different manners, such as chemical synthesis, synthesis by polymerization or by extraction of said gene starting with a source of nucleic acids.

The in vitro recombination of the polynucleotide sequences of the initial library by the process of the invention therefore permits the obtaining of a new library containing sequences having acquired one or several characteristics of the sequences of the previous library. The process of the invention therefore comprises an in vitro technique of evolution.

The process of the invention comprises an alternative to recombinant PCR such as implemented in the techniques of DNA shuffling (12) or of StEP (14), since it does not require the in vitro polymerization step in order to end up with the recombination. To the contrary, the key step of the process of the invention is the step (d) of ligation on an assembling template, which assures a very high degree of faithfulness in the course of the recombination events.

The process of the invention is notable in that it permits a considerable increase in the efficiency of the reassembling of the fragments to ligate. In effect, in the case of a sequence cut up into n fragments, there exists n" possibilities of reassociation of the fragments by using a classical process of ligation (without using a reassembling template which directs the ligation), among which a single form is of interest. In the case of the process of the invention, the ligation is directed by the assembling template, which permits to direct obtention of the single form of interest.

The fragmenting of these polynucleotide sequences at step (a) can be done either in a controlled manner or in a random manner.

In the case of a fragmenting carried out in a controlled manner, the fragmenting permits controlling with precision the degree of desired recombination and the position of the points of recombination. According to a preferred embodiment of the process of the invention, step (a) consists of subjecting the polynucleotide sequences of the library to hydrolysis by the action of one or several restriction enzymes. In this way, in one particular embodiment of the process of the invention, the degree of recombination and the position of the points of recombination of the recombined polynucleotide sequences are determined by the fragmenting of step (a).

Thus, the larger the number of fragments generated by the sequence, the higher the number of fragments necessary to recompose a sequence, which leads to a higher rate of recombination. Moreover, the nature and the position of the ends of the fragments generated in this embodiment of the process of the invention can be known and controlled, which permits:

controlling with precision the zones where the recombination takes place, or inducing recombination between polynucleotide sequences, for example genes, if the ends of the fragments are created in zones of homology between these sequences, or in zones of homology between these sequences and the assembling template or templates.

In the case of a random fragmenting, any enzymatic or mechanical means known to a person skilled in the art allowing a random cutting of the double-stranded DNA can be used, such as for example DNAse I digestion or sonication.

The process of the invention, which permits a considerable increase in the efficiency of reassembling fragments to be ligated, can therefore be applied to the directing of blunt end multi-molecular ligation. In this application, single or double-stranded oligonucleotides complementary only to the 3' end of a fragment and 5' of the adjacent fragment are used as the assembling template in steps (b) or (c), which permits adjacent hybridization of these two ends on the same template after the denaturation step. Once hybridized, the ends of the fragments can be ligated so as to direct the direction of the ligation of the blunt ended fragments. The same approach can be contemplated for the positioning of the ligation of fragments having sticky ends.

An especially preferred embodiment of the process of the invention consists of adding at step (c) and/or at step (d) enzymes capable of recognizing and of cutting in a specific manner the non-hybridized ends of fragments, when these overlap with other hybridized fragments on the same template. A preferred example of this type of enzyme is the Flap endonuclease enzyme (10).

A particular embodiment of the process of the invention therefore consists of using enzymes of the Flap endonuclease type when the fragments generated at step (a) can be overlapping during the hybridization on the assembling template (of) at step (c).

In this way, during the hybridization of single stranded DNA fragments on a template, these enzymes have the property of recognizing and of cutting, in a specific manner, the non-hybridized ends of these fragments, when they overlap with other hybridized fragments on the same template. In the course of the hybridization step (c), these enzymes therefore permit increasing the number of adjacent ends that can be ligated at step (d), which is particularly important in the case of fragments obtained by random cutting, as these fragments have zones overlapping with each other when they are hybridized on the assembling template.

In a particular embodiment of the process of the invention using a ligase active at high temperature and preferably thermostable at step (d), the endonucleases, capable of recognizing and of cutting in a specific manner the non-hybridized ends of the fragments such as the Flaps, added at step (c) and/or at step (d) will have the same properties of thermoresistance and of high temperature activity as said ligase.

The library of polynucleotide sequences on which the process of the present invention is carried out can be generated by any method known to a person skilled in the art, for example starting with a wild type gene, by successive steps of directed mutagenesis, by "error prone" PCR (2), by random chemical mutagenesis, by random in vivo mutagenesis, or by combining genes of close or distinct families within the same species or different species so as to obtain a variety of polynucleotide sequences in said library.

Among these techniques, the invention more particularly contemplates a process in which the library of double-stranded polynucleotide sequences is obtained by a polymerization chain reaction carried out under conditions that permit creation of random point mutations.

The initial library of double-stranded polynucleotide sequences can be composed of synthetic sequences which will be fragmented at step (a) or which can be the fragments of step (a).

According to a preferred embodiment for carrying out the process of the invention, step (a) consists of subjecting the polynucleotide sequences of the library to hydrolysis by the action of one or several restriction enzymes.

In order to increase the degree of recombination generated by the process of the invention, it is sufficient to increase the number of restriction fragments by using restriction enzymes having a large number of cutting sites on the polynucleotide sequences of the library, or by combining several restriction enzymes. In the case of using a thermostable and thermoactive ligase, the size of the smallest fragment thus generated will advantageously be greater or equal to 40 bp, in order to retain a hybridization temperature compatible with that of the ligation step (d) which is generally of the order of 65° C.

Step (a) can also be carried out by generating a library of fragments by random enzymatic or mechanical treatment. In particular, step (a) can consist of a random treatment with DNAse I of a library of partially heterologous double-stranded polynucleotide sequences. In the case where a random enzymatic or mechanical fragmenting is used in step (a), this embodiment of the process of the invention has the characteristic of permitting the use of fragments generated by this treatment as templates for each other, for the hybridization in the course of step (c) or of the RLR reaction of the steps (c) and (d) simultaneously.

Step (b) can be carried out by combining at least two distinct libraries of fragments separately generated at step (a) starting from the same initial library by different treatments, as for example with different restriction enzymes. In the case of the embodiment of such libraries, the fragments obtained at step (a) are used as templates for each other, for the hybridization during the course of step (c) or the RLR reaction of steps (c) and (d) simultaneously.

The fragments of step (a) of the process of the invention can be equally generated by amplification reactions such as PCR realized on the polynucleotide sequences of the library. Two solutions are contemplated. In a first case, the oligonucleotide primers can be conceived in a manner so as to generate fragments having ends which are adjacent all along the length of the assembling sequence. In a second case, the oligonucleotide primers are conceived in a fashion so as to generate fragments having common sequences, these fragments being capable of serving as an assembling template for each other at step (b) or at step (c). The process of the invention permits the combining in a random manner of different fragments obtained at step (a) and of reassembling them during steps (b), (c) and (d) within a polynucleotide sequence. This process therefore reproduces in vitro the recombination phenomena which can occur in vivo by favoring them. The process of the invention is therefore particularly of interest above all for recombining polynucleotide sequences among themselves in order to generate new polynucleotide sequences having interesting properties as compared to the corresponding properties of the reference sequences.

The effectiveness of the recombination of the process of the invention depends on the number of fragments generated by a polynucleotide sequence at step (a). Consequently, the process of the invention will use polynucleotide sequences having been fragmented into n fragments, n advantageously being greater or equal to three.

The assembling template of step (b) or (c) is for example a polynucleotide sequence coming from the initial library or a consensus sequence of said library, single or double-stranded. In the case where the assembling template is incorporated directly at step (c) of the invention, this template must be single-stranded.

According to a variant of the process of the invention, the assembling templates of steps (b) or (c) are composed of single or double-stranded oligonucleotides.

According to a particular embodiment of the process of the invention, oligonucleotides, single or double-stranded, of variable length, are added at step (b) or (c) in addition to the template. These oligonucleotides are designed (to be capable of being) so as to be substituted for a portion of the fragments of step (c), in effect, their sequence is such that:

if they are perfectly homologous with the sequence of the fragment which they are replacing, they favor certain combinations, or if they are partially heterologous with the sequence of the fragment that they are replacing, they introduce one or a more directed supplemental mutations.

Before step (e) of the process of the invention, it is possible to separate the recombined polynucleotide sequences from the assembling template thanks to a labeling present in the assembling template or in the recombined polynucleotide sequences. It is in effect possible to label each strand of the template according to techniques known to a person skilled in the art. For example, the label of the assembling template can be a hapten and the recombined polynucleotide sequences template are separated from the assembling template by techniques known to a person skilled in the art, such as for example an anti-hapten antibody boundon a support or a biotin-streptavidine reaction, if the hapten is a biotin label.

Other techniques can be employed in order to separate the recombined polynucleotide sequences from the assembling template. The assembling template can also be prepared specifically in a way so as to facilitate its elimination at the end of the process of the invention. It can thus be synthesized by PCR amplification using methylated dATP, which permits its degradation by the restriction endonuclease Dpn I. In this case, the recombined polynucleotide sequences must not contain methylated dATP. The template can also have been prepared by PCR amplification by using dUTP, which permits its degradation by treatment with a uracyl-DNA-glycosylase. Conversely, it is possible to protect the recombined polynucleotide sequences by amplifying them by selective PCR with oligonucleotides having 5' phosphorothioate groups. A treatment with an exonuclease then permits the specific digestion of the assembling template.

The process of the invention can include before the possible cloning of step (e), a step of amplification of the recombined polynucleotide sequences. Any amplification technique is acceptable, notably a PCR amplification. One of the most simple consists of carrying out a PCR which permits specific amplification of the recombined polynucleotide sequences owing to primers which can only be hybridized at the ends of the recombined sequences. The PCR products are then cloned in order to be characterized and the polynucleotide sequences having advantageous properties as compared to the corresponding properties of the reference sequences are selected.

The invention has for its object the generation of polynucleotide sequences liable to have advantageous properties as compared to the corresponding properties of reference sequences. The recombed polynucleotide sequences obtained at step (d) and possibly cloned are screened by any appropriate means in order to select the recombined polynucleotide sequences or the clones having advantageous properties as compared to the corresponding properties of the reference sequences. By advantageous property is understood to be, for example, the thermostability of an enzyme or its ability to function under conditions of pH or of temperature or of saline concentration more adapted to an enzymatic process than the control proteins usually used for said process. For example, such a process can be an industrial process to breakdown textile fibers or bleaching paper pulps or producing flavors in the dairy industry, the processes of biocatalysis for the synthesis by an enzymatic pathway of new therapeutic molecules, etc.

According to an advantageous embodiment of the process of the invention, the polynucleotide sequence library can therefore be the result of a screening having permitted selection by any appropriate means of polynucleotide sequences having advantageous properties as compared to control sequences. The sequences selected in this way comprise a limited library.

But, it is also possible to start from a non-limited library in order to preserve the representation of the properties contained in that library.

The sequences coding for the protein or proteins having one or more advantageous properties as compared to the reference proteins are thus selected, by in vivo or in vitro screenings, and can be used to form a new library for a possible repeating of the process of the invention. One advantageous embodiment of the process of the invention therefore consists of using as the library several polynucleotide sequences selected after a first implementation of the process of the invention, possibly mixed with other polynucleotide sequences. Among the screening techniques which can be applied to each of the clones of step (e), the screening techniques in vitro give rise to the advantage of being free of problems of cellular physiology, and of any drawbacks tied to the in vivo expression cloning. Moreover, this type of screening is easily automated, which permits screening a higher number of recombined polynucleotide sequences.

The invention also relates to a recombined polynucleotide sequence obtained by a process according to the invention, as well as to a vector containing such a recombined polynucleotide sequence, a cellular host transformed by a recombined polynucleotide sequence or by a vector of the invention, as well as a protein coded by this recombined polynucleotide sequence. The invention includes as well the corresponding libraries of recombined polynucleotide sequences, vectors, cellular hosts, or proteins.

Other advantages and features of the invention will appear from the examples of carrying out the invention, which follow and which are referred to in the attached drawings in which:

FIG. 3 represents the positions of the ten zones of mutations (Pvu II and Pst I) carried by each mutant of the ponB gene used for the examples of the implementation of the invention.

FIG. 4 represents the position of the primers used as compared to the sequence of the ponB gene.

FIG. 5 represents the migration on agarose gel of RLR and of PCR reaction products of these RLR reactions.

FIG. 6 represents the position of the mutations as compared to the restriction fragments.

I—EXAMPLE

Figure 1:
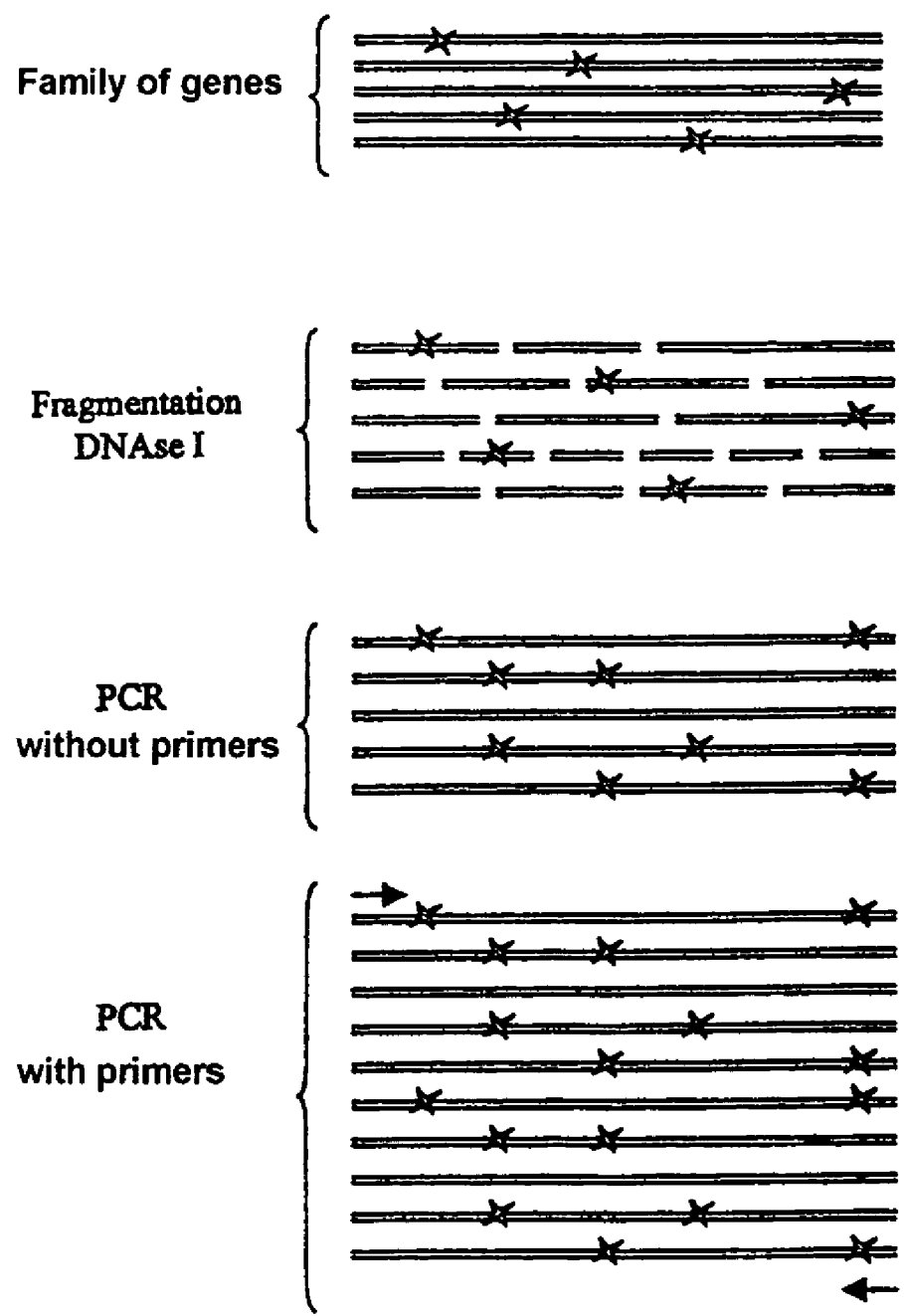
FIG. 1 is a schematic representation of the processes of the prior art corresponding respectively to DNA-shuffling (FIG. 1A) and to StEP (FIG. 1B).
Figure 2:
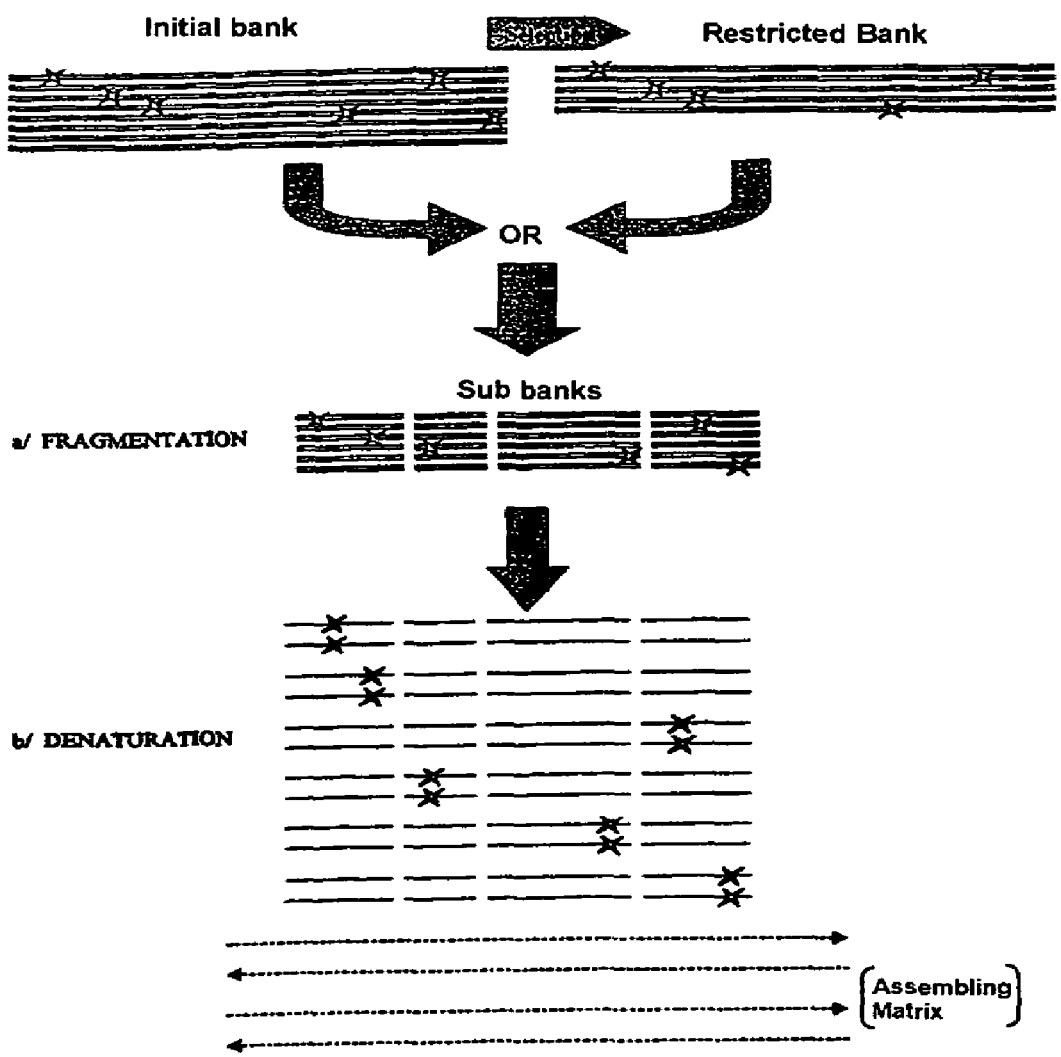
FIG. 2 is a schematic representation of an example of carrying out the process of the invention and of certain of its variations and applications.

The process of the invention was put into practice starting from a library of gene mutants of ponB, coding for the PBP1b of *E. coli* (1). Ten mutants of this gene were used. The gene sequence of each mutant differs from that of the native gene by a non homologous zone of thirteen to sixteen bases in length resulting from the substitution of five initial codons by five alanine codons according to the technique described by Lefèvre et al. (8).

The substitution carried by each mutant is characterized by the presence of a unique site of the restriction enzyme Pvu II surrounded by two Pst I enzyme sites, which permits the mutants to be distinguished from each other by their digestion profile with these restriction endonucleases. FIG. 3 represents the positions of the ten zones of mutations (Pvu II and Pst I) carried by each mutant.

After PCR amplification of the genes of the ten mutants, the PCR products were purified, mixed in equimolar quantity in order to form the library. The polynucleotide sequences of this library were digested with the restriction enzymes Hinf I and Bsa I, in such a way as to generate libraries of restriction fragments. The restriction fragments were then incubated with various amounts of the wild type template, at different quantities, in the presence of a thermostable ligase. After several denaturation/hybridization/ligation cycles, a fraction of the reaction mixture was used to carry out a PCR amplification with a couple of primers specific to the 5' and 3' ends of the genes of the mutants and non-specific to the 5' and 3' ends of the wild type template. The amplification product was cloned and the obtained clones were analyzed for their digestion profile with the Pvu II or Pst I restriction endonucleases. The obtained profiles permitted the determination of which fragment(s) of the mutants had been able to be recombined with the others in order to form an entire gene.

II MATERIALS

1) Strains and Plasmids

The strain MC1061 (F$^-$ araD139, Δ (ara-leu)7696, galE15, galK16, Δ (lac)X74, rpsL (Str$^R$), mcrA mcrB1, hsdR2 ($r_k^-$ $m_k^+$)) is derived from *Escherichia coli* K12.

The vector pARAPONB stems from the vector pARA13 (3) in which the ponB gene carrying a thrombin-cutting site (9) was introduced between the restriction sites Nco I and Nar I. The vector pET26b+ is one of the pET vectors developed by Studier and Moffatt (13) and commercialized by NOVAGEN Corporation.

2) Oligonucleotides

The oligonucleotides were synthesized by ISOPRIM corporation (Toulouse). The oligonucleotide sequences are reported in Table I below.

TABLE I

| Oligo N | 5' ACTGACTACCATGGCCGGGAATGACCGCGAGCC 3' (SEQ ID NO:1) |
|---|---|
| Oligo E | 5' CCGCGGTGGAGCGAATTCTAATTACTACCAAACATA TCC 3' (SEQ ID NO:2) |
| Oligo M1 | 5' GCGCCTGAATATTGCGGAGAAAAAGC 3' (SEQ ID NO:3) |
| Oligo M2 | 5' ACAACCAGATGAAAAGAAAGGGTTAATATC 3' (SEQ ID NO:4) |
| Oligo A1 | 5' ACTGACTACCATGGCC 3' (SEQ ID NO:5) |
| Oligo A2 | 5' CCGCGGTGGAGCGAATTC 3' (SEQ ID NO:6) |

3) Reagents

The restriction and modification enzymes cited in Table II below were used according to the recommendations of the suppliers.

TABLE II

| Enzyme | Concentration | Supplier |
|---|---|---|
| NcoI | 10 U/μl | New England Biolabs |
| PstI | 20 U/μl | New England Biolabs |

TABLE II-continued

| Enzyme | Concentration | Supplier |
|---|---|---|
| Eco RI | 20 U/µl | New England Biolabs |
| Bsa I | 5 U/µl | New England Biolabs |
| Hinf I | 10 U/µl | New England Biolabs |
| Pvu II | 10 U/µl | New England Biolabs |
| T4 DNA ligase | 400 U/µl | New England Biolabs |
| Taq DNA polymerase | 5 U/µl | PROMEGA |
| AMPLIGASE | 100 U/µl | EPICENTRE |

The buffers used are reported in Table III below

| Buffers | Composition |
|---|---|
| T | Tris HCl 10 mM, pH 8.0 |
| Polymerization 20× | Tris HCl 100 mM pH 8.3, MgCl$_2$ 15 mM, KCl 500 mM, 1.0% TRITON X100 ® |
| Restriction A 10× | 500 mM NaCl, 100 mM Tris HCl pH 7.9, 100 mM MgCl$_2$, 10 mM DTT |
| Restriction B 10× | 1 M NaCl, 500 mM Tris HCl pH 7.9, 100 mM MgCl$_2$, 10 mM DTT |
| Restriction C 10× | 500 mM NaCl, 1 M Tris HCl pH 7.5, 100 mM mM MgCl$_2$, 0.25% TRITON X100 ® |
| AMPLIGASE 10× | 200 mM Tris HCl pH 8.3, 250 mM KCl, 100 mM MgCl$_2$, 5 mM NAD, 0.1% TRITON X100 ® |
| Ligation 10× | 500 mM Tris HCl pH 7.5, 100 mM MgCl$_2$, 100 mM DTT, 10 mM ATP, 250 µg/ml BSA |

III PREPARATION OF THE TEMPLATE

The wild type ponB gene was amplified by a PCR reaction step by using as primers the oligonucleotides M1 and M2 (FIG. 4). Five PCR reactions were prepared by adding 50 ng of pPONBPBR plasmid carrying the wild type gene (7) to a mixture containing 10 µl of polymerization buffer, 10 µl of dNTPs 2 mM, 20 pmol of each oligonucleotide M1 and M2, and 5 U of Taq DNA polymerase, in a final volume of 100 µl. These mixtures were incubated in Perkin-Elmer 9600 Thermocycler according to the following program: (94° C.-2 min.)–(94° C. 15 sec.-60° C. 30 sec.-72° C. 1 min.)×29 cycles-(72° C.-3 min.).

The product of the five PCR was mixed and loaded on a 1% TBEagarose gel after migration and staining of the gel with ethidium bromide, the band at 2651 bp, corresponding to the ponB gene amplification product surrounded by two fragments of 26 bp and 90 bp respectively, was visualized by trans-illumination under ultraviolet, and cut out with a scalpel in order to be purified with the QIAquick system (QIAGEN). All the DNA thus eluted was eluted in 120 µl of buffer T. The concentration of this DNA was approximately 100 ng/µl as measured by its absorbance at 260 nm.

IV PREPARATION OF THE LIBRARY

1) Amplification of the Mutant Genes

The genes of the ten mutants were separately amplified by a PCR reaction with oligonucleotides N and E. These oligonucleotides introduce respectively the restriction sites Nco I and Eco RI, permitting the cloning of the products obtained with these two sites.

Each PCR reaction was prepared by adding 50 ng of the plasmid carrying the mutant gene to a mixture containing 10 µl of polymerization buffer, 10 µl of dNTPs 2 mM, 20 pmol of each oligonucleotide N and E, and 5 U of Taq DNA polymerase, in a final volume of 100 µl. This mixture was incubated in a Perkin-Elmer 9600 thermocycler according to the following program: (94° C.-2 min.)–(94° C. 15 sec.-60° C. 30 sec.-72° C. 1 min.)×29 cycles-(72° C.-3 min.).

The specificity of the genetic amplification was verified by restriction profile with the Pvu II endonuclease, by incubating 5 µl of each PCR product 1 hour at 37° C. in a mixture containing 3 µl of restriction buffer A and 5 U of the Pvu II enzyme in a final volume of 30 µl. 15 µl of that digestion reaction were loaded on a TBE 1% agarose gel. After migration and staining with ethidium bromide, the gel was exposed to ultraviolet. The visualization of the restriction fragments permitted confirmation of the specificity of the genetic amplification of each mutant gene.

In parallel, 3 µl of each PCR reaction were loaded on a TBE 1% agarose gel. After migration, the gel was treated as above. The intensity of each band permitted the assessment that the genetic amplifications had the same yield.

2) Creation of Libraries of Restriction Fragments.

50 µl of each of the ten PCR were mixed and loaded on a 1% TBE agarose gel. After migration and staining with ethidium bromide, the band at 2572 bp, corresponding to the amplification product of the genes of the ten mutants, was cut out with a scalpel and purified with the QIAquick system (QIAGEN). All the DNA thus purified was eluted in 120 µl of buffer T. The concentration of this DNA was approximately 100 ng/µl according to its absorbance at 260 nm.

In order to generate the libraries of restriction fragments, 100 µl of this DNA were incubated for one hour at 50° C. in a mixture containing 12 µl of restriction buffer B, 1.2 µl of BSA (at 10 mg/ml), 25 U of the enzyme Bsa I and 4 µl of water. Then, 2 µl of restriction buffer B, 2 µl of BSA (at 1 mg/ml), 50 U of the enzyme Hinf I and 11.5 µl of water were added to the mixture, which was incubated for one hour at 37° C. The digestion mixture was purified on a QIAquick column (QIAGEN), and eluted with 30 µl of buffer T. 1 µl of this eluate was loaded on a 1% TBE agarose gel in order to verify that the digestion had been total, and that it had generated 6 restriction fragments, and consequently six libraries of fragments, of 590 bp, 500 bp, 472 bp, 438 bp, 298 bp and 274 bp. The concentration of this DNA was approximately 250 ng/µl according to its absorbance at 260 nm.

V RLR (RECOMBINING LIGATION REACTION).

The RLR reaction (Recombining Ligation Reaction) was carried out by incubating determined quantities of restriction fragments Hinf I-Bsa I from the genes of ten mutants with the complete template (i.e., the wild type ponB gene), in the presence of a thermostable DNA ligase. The table IV below reports the composition of the mixtures for RLR.

TABLE IV

|  | RLR 1 | RLR 2 | RLR 3 | RLR 4 | T- |
|---|---|---|---|---|---|
| Fragments Hinf I - Bsa I of ten mutants (100 ng/µl) | 0.5 µl | 1 µl | 2 µl | 5 µl | 5 µl |

TABLE IV-continued

|  | RLR 1 | RLR 2 | RLR 3 | RLR 4 | T- |
|---|---|---|---|---|---|
| Wild type ponB template (100 ng/µl) | 0.6 µl | 1.2 µl | 2.4 µl | 6 µl | 6 µl |
| AMPLIGASE 10× Buffer | 2 µl | 2 µl | 2 µl | 2 µl | 2 µl |
| AMPLIGASE (25 U/µl) | 1 µl | 1 µl | 1 µl | 1 µl | — |
| H₂O | qsp 20 µl | qsp 20 µl | qsp 20 µl | qsp 20 µl | qsp 20 µl |

The negative control is identical to the reaction of RLR4, but does not contain thermostable DNA ligase. These different mixtures were covered with a drop of mineral oil and incubated in a Perkin-Elmer 9600 thermocycler in 200 µl microtubes according to the following program: (94° C., 5 min.)–(94° C., 1 min.-65° C., 4 min.)×35 cycles.

10 µl of each RLR reaction were then added to a PCR reaction mixture containing 10 µl of polymerization buffer, 10 µl of 2 mM dNTPs, 40 pmol of each oligonucleotide A1 and A2, and 5 U of Taq DNA polymerase in a final volume of 100 µl. This mixture was incubated in a Perkin-Elmer 9600 thermocycler according to the following program: (94° C., 5 min.)–(94° C., 30 sec.-46° C., 30 sec.-72° C., 1 min.)×29 cycles–(72° C., 2 min.). This PCR reaction permitted specific amplification of the ligation products formed in the course of the RLR reaction, without amplifying the template, since the oligonucleotides A1 and A2 are not able to hybridize with the template (it), as shown in FIG. 4.

5 µl of each RLR reaction and 10 µl of each of the previous PCR reactions were loaded on a 1% TBE agarose gel. After staining with ethidium bromide, the gel was exposed to ultraviolet light, as shown in FIG. 5.

The analysis of this gel reveals that only the reaction of RLR4 contains, as the negative control, restriction fragments still visible (tracks 4 and 5).

The absence of PCR product for the negative control (track 10) reveals not only that the PCR reaction is specific (no amplification of the complete template), but also that the restriction fragments present in the mixture cannot be substituted for the primers to generate a contaminant PCR product under the chosen conditions. In parallel, the presence of a unique band at about 2500 bp in tracks 6, 7 and 8 demonstrates that an RLR product was able to be amplified by PCR for the RLR1, 2 and 3 reactions. These three RLR reactions therefore permitted the regeneration of one or more of the complete genes starting from six libraries of restriction fragments.

VI ANALYSIS OF THE AMPLIFICATION PRODUCTS OF THE RLR REACTIONS

1) Cloning

The PCR amplification products of the RLR 1, 2 and 3 reactions were purified with the WIZARD PCR PREPS system (PROMEGA) and eluted in 45 µl of buffer T. 6 µl of each purified PCR were incubated 1 hour at 37° C. in a mixture containing 3 µl of restriction buffer C, 3 µl of BSA (1 mg/ml), 20 U of the Eco RI enzyme, 10 U of the Nco I enzyme and 15 µl of water.

In parallel, two vectors (pARAPONB and pET26b+) were prepared for the cloning. These vectors were linearized by incubating 3 µg of these plasmids for 2 hours at 37° C., in a mixture containing 3 µl of restriction buffer C, 3 µl of BSA (1 mg/ml), 20 U of the Eco RI enzyme, 10 U of the Nco I enzyme and 19 µl of water.

The linearized vectors as well as the digested PCR were purified on a TBE 1% agarose gel with the QIAquick system (QIAGEN). Each vector or each digested PCR was eluted in 30 µl of buffer T.

The ligation of each PCR digested with each of the vectors was carried out according to the conditions described in table V below, and incubated at 16° C. for 16 hours.

TABLE V

|  | Ligation with the vector pARAPONB | | | | Ligation with the vector pET26b+ | | | |
|---|---|---|---|---|---|---|---|---|
|  | LpAR1 | LpAR2 | LpAR3 | TLpAR | LpET1 | LpET2 | LpET3 | TLpET |
| PCR amplification RLR 1 digested Nco I - Eco RI | 4 µl | — | — | — | 4 µl | — | — | — |
| PCR amplification RLR 2 digested Nco I - Eco RI | — | 4 µl | — | — | — | 4 µl | — | — |
| PCR amplification RLR 3 digested Nco I - Eco RI | — | — | 4 µl | — | — | — | 4 µl | — |
| Vector pARAPONB digested Nco I - Eco RI | 1 µl | 1 µl | 1 µl | 1 µl | — | — | — | — |
| Vector pET26b+ digested Nco I - Eco RI | — | — | — | — | 1 µl | 1 µl | 1 µl | 1 µl |
| Ligation Buffer | 2 µl | 2 µl | 2 µl | 2 µl | 2 µl | 2 µl | 2 µl | 2 µl |
| Ligase | 1 µl | 1 µl | 1 µl | 1 µl | 1 µl | 1 µl | 1 µl | 1 µl |
| H₂O | 12 µl | 12 µl | 12 µl | 16 µl | 12 µl | 12 µl | 12 µl | 16 µl |

200 µl of chimiocompetent MC1061 cells (4) were transformed with 10 µl of each ligation by a thermal shock (5), and the cells thus transformed were spread over a selection medium.

No clone was obtained after transformation of ligation controls TLpAR and TLpET, thus indicating that the Nco I-Eco RI vectors pARAPONB and pET26b+ cannot undergo an intramolecular ligation.

2) Screening by PCR

A first screening of the clones obtained after transformation of the ligations with the vector pARAPONB was carried out by PCR. 42 colonies, 14 from each ligation LpAR1, LpAR2 and LpAR3, were resuspended individually in a PCR mixture containing 5 µl of polymerization buffer, 40 pmol of each oligonucleotide A1 and A2, 5 µl of 2 mM dNTPs and 5 U of Taq DNA polymerase in a final volume of 50 µl. A negative control was obtained by adding to the PCR mixture 50 ng of the plasmid pBR322 in place of the colony. These 43 tubes were incubated in a Perkin-Elmer 9600 thermocycler according to the following program: (94° C., 5 min.)–(94° C., 30 sec.-46° C., 30 sec.-72° C., 1 min.)×29 cycles–(72° C., 2 min.). 5 µl of each of these PCR reactions were then incubated for 1 hour at 37° C. in a mixture containing 2 µl of restriction buffer A, 2 µl of BSA (1 mg/ml) and 5 U of the restriction enzyme Pvu II in a final volume of 20 µl.

10 µl of each of these digestions were loaded on a TBE 1% agarose gel in parallel with 5 µl of each non-digested PCR (thus avoiding possible confusion of non-specific bands of the PCR with a fragment obtained by restriction digestion). After migration and staining of this gel with ethidium bromide, the bands resulting from the digestion by the enzyme Pvu II were analyzed in order to determine which fragment(s) of initial mutants was/were associated with the others in order to reconstruct an entire gene. This screening reveals the presence of 27 genes carrying one mutation, 7 genes carrying two mutations and 8 genes no longer carrying any mutation.

3) Screening by Plasmidic DNA Minipreparation

The second screening was effected by carrying out an extraction of the plasmidic DNA (5) from 21 clones resulting from the transformation of the ligations with the vector pET26b+ (7 clones of each ligation). 5 µl of the plasmidic DNA thus obtained for each clone were incubated for 1 hour at 37° C. in a mixture containing 1 µl of restriction buffer C, 6 U of the enzyme Pst I, 3 U of the enzyme Nco I and 6 U of the enzyme Eco RI in a final volume of 10 µl. 5 µl of each of these digestions were loaded on a TBE 1% agarose gel. After migration and staining of this gel with ethidium bromide, the bands resulting from the digestion by the Pst I enzyme were analyzed in order to determine which fragment(s) of the initial mutants had associated with the others in order to reconstruct an entire gene. This screening reveals the presence of 13 genes carrying a mutation, 5 genes carrying two mutations and 3 genes no longer carrying a mutation.

4) Statistical Analysis of the Recombinations.

According to the position of each mutation as compared to the cutting sites of the enzymes Hinf I and Bsa I, as represented in FIG. 6, it is possible to calculate the probability of obtaining in the course of the RLR reaction the creation of a gene carrying 0, 1, 2, 3, or 4 of the mutations of the initial genes.

Thus, by considering that the RLR reaction is totally random the probabilities P are as follows:

$$P(0 \text{ mutation}) = \prod_{i=6}^{9}\left(\frac{i}{10}\right) = 30.24\%$$

$$P(1 \text{ mutation}) = \sum_{n=1}^{4}\left[\frac{n}{10-n}\prod_{i=1}^{4}\left(\frac{10-i}{10}\right)\right] = 44.04\%$$

$$P(2 \text{ mutations}) = \sum_{n=1}^{4}\left[\sum_{a=1}^{4-n}\left(\frac{10-a}{a}\right)\left(\frac{10-(a+n)}{a+n}\right)\prod_{i=1}^{4}\left(\frac{i}{10}\right)\right] = 21.44\%$$

$$P(3 \text{ mutations}) = \sum_{n=1}^{4}\left[\left(\frac{10-n}{n}\right)\prod_{i=1}^{4}\left(\frac{i}{10}\right)\right] = 4.04\%$$

$$P(4 \text{ mutations}) = \prod_{i=10}^{4}\left(\frac{i}{10}\right) = 0.24\%$$

The two screenings carried out give results close to these statistical predictions, as reported in table VI below, thus indicating that the RLR reaction is quasi-random. A slightly higher proportion of genes carrying one mutation, to the detriment of the genes carrying zero mutation, is observed. This phenomenon could be attributed to a weak toxicity of the ponB gene already observed and to the slight of expression leakage of vectors pARAPONB and pET26b+, which would favor the selection of genes carrying an inactivating mutation.

TABLE IV

| | % | | | | |
|---|---|---|---|---|---|
| | 0 mutation | 1 mutation | 2 mutations | 3 mutations | 4 mutations |
| Statistics | 30.24 | 44.04 | 21.44 | 4.04 | 0.24 |
| PCR Screening | 21 | 63 | 16 | 0 | 0 |
| Mini-preparation Screening | 14 | 62 | 24 | 0 | 0 |

Biographical References

1) Broome-Smith J. K., Edelman Al, Yousif S. and Spratt B. G., (1985), The nucleotide sequence of the ponA and ponB genes encoding penicillin-binding proteins 1A and 1B of *Escherichia coli* K12, Eur. J. Biochem., 147, 437-446.
2) Caldwell R. C. and Joyce G., 1992, Randomization of genes by PCR mutagenesis, PCR Methods and Application, 2, 28-33.
3) Cagnon C., Valverde V. and Masson J.-M., (1991), A new family of sugar inducible expression vectors for *Escherichia coli*, Prot. Eng., 4, 843-847.
4) Hanahan D., (1985), Techniques for transformation of *Escherichia coli*, in DNA cloning: a practical approach, Glover D. M. (ed), IRL Press, Oxford vol I, 109-135.
5) Maniatis T., Fristch E. F. and Sambrook J., (1982), Molecular cloning. A laboratory Manual, Cold Spring Harbor Laboratory, Cold Spring Harbor, N.Y.
6) Landt et al., Gene, 96, 125-128, 1990.
7) Lefèvre F., Topological Analysis of the Penicillin Binding Protein 1b of *Escherichia coli*, 1997, Thèse.
8) Lefèvre F., Rémy M. H. and Masson J. M., 1997 (a), Alanine-stretch scanning mutagenesis: a simple and efficient method to probe protein structure and function, Nuc. Acids Res., 25, 447-448.

9) Lefèvre F., Rémy M. H. and Masson J. M., 1997 (b), Topographical and functional investigation of *Escherichia coli* Penicillin-Binding Protein 1b by alanine stretch scanning mutagenesis, J. Bacteriol., 179, 4761-4767.

10) Lyamichev V., Mast A. I., Prudent J. R., Kaiser M. W., Takova T., Kwiatkowski R. W., Sander T. J., de Arruda M., Arco D. A., Neri B. P. and Brown M. A. D., 1999, Polymorphism identification and quantitative detection of genomic DNA by invasive cleavage of oligonucleotide probes, Nature Biotechnology, 17, 292-296.

11) Picard et al., Nuc. Acids Res., 22, 2587-2591, 1994.

12) Stemmer W. P. C., (1994), Rapid evolution of a protein in vitro by DNA shuffling, Nature, 370, 141-144.

13) Studier F. W. and Moffatt B. A., 1986, Use of bacteriophage T7 RNA polymerase to direct selective high-level expression of cloned genes, J. Mol. Biol, 189, 113-130.

14) Zhao, H., Giver L., Shao Z., Affholter J. A. and Arnold F., 1998, Molecular evolution by staggered extension process (StEP) in vitro recombination, Nature Biotech., 16, 258-261.

What is claimed is:

1. A recombined polynucleotide library produced from an initial library of polynucleotide fragments comprising the steps of:
   (a) hybridizing the fragments to an assembly template;
   (b) ligating together the hybridized fragments that have adjacent ends with a ligase;
   (c) denaturing the ligated fragments from the assembly template; and
   (d) repeating at least the hybridizing, ligating and denaturing steps multiple times;
   wherein said recombined polynucleotide library:
   1) is obtained without the use of polymerase in steps (a) to (d),
   2) comprises only the fragments present in the initial library of polynucleotide fragments and sequences having one or several properties of the sequences of the initial library, and
   3) comprises randomly recombined polynucleotides comprising said ligated fragments.

2. A recombined polynucleotide library produced from an initial library of polynucleotide fragments comprising the steps of:
   (a) hybridizing, to an assembly template, fragments of polynucleotides derived from the initial library of polynucleotide fragments comprised of at least two different polynucleotides;
   (b) ligating together the hybridized fragments that have adjacent ends with a ligase;
   (c) denaturing the ligated fragments from the assembly template; and
   (d) repeating at least the hybridizing, ligating and denaturing steps multiple times, thereby forming random recombinant polynucleotides comprised of ligated fragments;
   wherein said recombined polynucleotide library:
   1) is obtained without the use of polymerase in steps (a) to (d),
   2) comprises only the fragments present in the initial library of polynucleotide fragments and sequences having one or several properties of the sequences of the initial library, and
   3) comprises randomly recombined polynucleotides comprising said ligated fragments.

3. A recombined polynucleotide library derived from an initial library of polynucleotide sequences comprising ligated fragments of said initial library of polynucleotide sequences, said fragments being aligned in accordance with a complementary assembly template, wherein the recombined polynucleotide library comprises only the fragments present in the initial library of polynucleotide sequences, said recombined polynucleotide library includes at least one recombined sequence having one or several properties of the sequences of the initial library, and wherein said recombined polynucleotide library comprises randomly recombined polynucleotides comprising said ligated fragments.

* * * * *